(12) United States Patent
Vermeij

(10) Patent No.: US 7,807,184 B2
(45) Date of Patent: Oct. 5, 2010

(54) HYBRID SHIGA-LIKE TOXIN

(75) Inventor: Paul Vermeij, St. Anthonis (NL)

(73) Assignee: Interuet International B.V., Boxmeer (NL)

( * ) Notice: Subject to any disclaimer, the term of this patent is extended or adjusted under 35 U.S.C. 154(b) by 1234 days.

(21) Appl. No.: 10/565,183

(22) PCT Filed: Jul. 16, 2004

(86) PCT No.: PCT/EP2004/051522

§ 371 (c)(1),
(2), (4) Date: Jan. 18, 2006

(87) PCT Pub. No.: WO2005/011733

PCT Pub. Date: Feb. 10, 2005

(65) Prior Publication Data

US 2008/0107653 A1 May 8, 2008

(30) Foreign Application Priority Data

Jul. 21, 2003 (EP) .................................. 03077266

(51) Int. Cl.
A61K 39/108 (2006.01)
A61K 39/02 (2006.01)
A61K 39/00 (2006.01)
A61K 39/38 (2006.01)
A61K 38/00 (2006.01)
C07K 14/00 (2006.01)

(52) U.S. Cl. .............. 424/257.1; 424/200.1; 424/192.1; 424/234.1; 424/184.1; 424/236.1; 424/832; 424/241.1; 514/2; 530/350; 530/825

(58) Field of Classification Search ........................ None
See application file for complete search history.

(56) References Cited

U.S. PATENT DOCUMENTS 6,019,973 A * 2/2000 Holmgren et al. ......... 424/185.1

FOREIGN PATENT DOCUMENTS

| EP | 1 057 895 A1 | 12/2001 |
|---|---|---|
| WO | WO 01/70945 A1 | 9/2001 |
| WO | WO 01/89456 A2 | 11/2001 |

OTHER PUBLICATIONS

Abhineet S. Sheoran et al., Stx2-Specific Human Monoclonal . . . , Infection and Immunity, Jun. 2003, p. 3125-3130, vol. 71 No. 6, American Society for Microbiology, US.

Jean Mukherjee et al., Human Stx2-Specific Monoclonal Antibodies . . . , Infection and Immunity, Feb. 2002, p. 612-619, vol. 70 No. 2, American Society for Microbiology, US.
David L. MacLeod et al., Purification and Characterization of an . . . , Infection and Immunity, May 1990, p. 1232-1239, vol. 58 No. 5, American Society for Microbiology, US.
Frances Pouch Downes et al., Affinity Purification and Characterization . . . , Infection and Immunity, Aug. 1988, p. 1926-1933, vol. 56 No. 8, American Society for Microbiology.
B. Wolfanger Belisle et al., Monoclonal Antibodies . . . , Infection and Immunity, Dec. 1984, p. 759-764, vol. 46 No. 3, American Society for Microbiology, US.
B. Wolfanger Belisle et al., Characterization of Monoclonal . . . , Infection and Immunity, Mar. 1984, p. 1027-1032, vol. 43 No. 3, American Society for Microbiology, US.
Claudia Jemal et al., Analysis of Shiga Toxin . . . , Journal of Bacteriology, Jun. 1995, p. 3128-3132, vol. 177 No. 11, American Society for Microbiology, US.
Angela R. Melton-Celsa et al., Activation of Shiga toxin . . . , Molecular Microbiology, 2002, p. 207-215, vol. 43 No. 1, Blackwell Science, Ltd.
Chiara Rodighiero et al., Structural Basis for . . . , The J. of Biological Chemistry, Feb. 12, 1999, p. 3962-3969, vol. 274 No. 7, Amer. Soc. for Biochemistry and Molecular Bio.
Michael Martin et al., Recombinant Antigen-Exterotoxin . . . , Infection and Immunity, Jan. 2001, p. 252-261, vol. 69 No. 1, American Society for Microbiology, US.
Michael G. Jobling et al., Fusion Proteins Containing . . . , Infection and Immunity, Nov. 1992, p. 4915-4924, vol. 60 No. 11, American Society for Microbiology, US.
Ethan A. Merritt et al., AB5 Toxins . . . Current Opinion in Structural Biology, 1995, p. 165-171, vol. 5, Current Biology Ltd.
James C. Paton et al., Pathogenesis and Diagnosis . . . , Clinical Micro. Reviews, Jul. 1998, p. 450-479, vol. 11 No. 3, American Society for Microbiology, US.
M. Lebens et al., Synthesis of Hybrid Molecules . . . , Infection and Immunity, Jun. 1996, p. 2144-2150, vol. 64 No. 6, American Society for Microbiology, US.

* cited by examiner

Primary Examiner—S. Devi
(74) Attorney, Agent, or Firm—William M. Blackstone; Aaron L. Schwartz

(57) ABSTRACT

The present invention relates to a hybrid bacterial toxin subunit, to a hybrid bipartite bacterial toxin and to nucleic acid molecules comprising a nucleotide sequence encoding such bacterial toxins. Furthermore, the invention relates to vaccines comprising bacterial toxins and to their use in vaccines. Finally, the invention relates to methods for the preparation of such vaccines and to the use of such bacterial toxins for the manufacture of such vaccines.

10 Claims, 3 Drawing Sheets

Figure 2

SEQUENCE LISTING

```
<160> NUMBER OF SEQ ID NOS: 8

<210> SEQ ID NO 1
<211> LENGTH: 1325
<212> TYPE: DNA
<213> ORGANISM: Escherichia coli
<220> FEATURE:
<221> NAME/KEY: CDS
<222> LOCATION: (1)..(954)

<400> SEQUENCE: 1 atg atg aag tgt ata ttg tta aag tgg ata ctg tgt ctg tta ctg ggt       48
Met Met Lys Cys Ile Leu Leu Lys Trp Ile Leu Cys Leu Leu Leu Gly
1               5                   10                  15 ttt tct tcg gta tcc tat tcc cag gag ttt acg ata gac ttt tcg act       96
Phe Ser Ser Val Ser Tyr Ser Gln Glu Phe Thr Ile Asp Phe Ser Thr
            20                  25                  30 caa caa agt tat gta tct tcg tta aat agt ata cgg aca gtg ata tcg      144
Gln Gln Ser Tyr Val Ser Ser Leu Asn Ser Ile Arg Thr Val Ile Ser
        35                  40                  45 acc cct ctt gaa cat ata tct cag gga gct aca tcg gta tcc gtt att      192
Thr Pro Leu Glu His Ile Ser Gln Gly Ala Thr Ser Val Ser Val Ile
```

-continued

```
             50                  55                  60
aat cat aca cca cca gga agt tat att tcc gta ggt ata cga ggg ctt      240
Asn His Thr Pro Pro Gly Ser Tyr Ile Ser Val Gly Ile Arg Gly Leu
 65              70                  75                  80 gat gtt tat cag gag cgt ttt gac cat ctt cgt ctg att att gaa cga      288
Asp Val Tyr Gln Glu Arg Phe Asp His Leu Arg Leu Ile Ile Glu Arg
             85                  90                  95 aat aat tta tat gtg gct gga ttt gtt aat acg aca aca aat act ttc      336
Asn Asn Leu Tyr Val Ala Gly Phe Val Asn Thr Thr Thr Asn Thr Phe
                100                 105                 110 tac aga ttt tca gat ttt gca cat ata tca ttg ccc ggt gtg aca act      384
Tyr Arg Phe Ser Asp Phe Ala His Ile Ser Leu Pro Gly Val Thr Thr
            115                 120                 125 att tcc atg aca acg gac agc agt tat acc act ctg caa cgt gtc gca      432
Ile Ser Met Thr Thr Asp Ser Ser Tyr Thr Thr Leu Gln Arg Val Ala
130                 135                 140 gcg ctg gaa cgt tcc gga atg caa atc agt cgt cac tca ctg gtt tca      480
Ala Leu Glu Arg Ser Gly Met Gln Ile Ser Arg His Ser Leu Val Ser
145                 150                 155                 160 tca tat ctg gcg tta atg gag ttc agt ggt aat aca atg acc aga gat      528
Ser Tyr Leu Ala Leu Met Glu Phe Ser Gly Asn Thr Met Thr Arg Asp
            165                 170                 175 gca tca aga gca gtt ctg cgt ttt gtc act gtc aca gca gaa gcc tta      576
Ala Ser Arg Ala Val Leu Arg Phe Val Thr Val Thr Ala Glu Ala Leu
        180                 185                 190 cgg ttc agg caa ata cag aga gaa ttt cgt ctg gca ctg tct gaa act      624
Arg Phe Arg Gln Ile Gln Arg Glu Phe Arg Leu Ala Leu Ser Glu Thr
    195                 200                 205 gct cct gtt tat acg atg acg ccg gaa gac gtg gac ctc act ctg aac      672
Ala Pro Val Tyr Thr Met Thr Pro Glu Asp Val Asp Leu Thr Leu Asn
210                 215                 220 tgg ggg aga atc agc aat gtg ctt ccg gag tat cgg gga gag gct ggt      720
Trp Gly Arg Ile Ser Asn Val Leu Pro Glu Tyr Arg Gly Glu Ala Gly
225                 230                 235                 240 gtc aga gtg ggg aga ata tcc ttt aat aat ata tca gcg ata ctt ggt      768
Val Arg Val Gly Arg Ile Ser Phe Asn Asn Ile Ser Ala Ile Leu Gly
                245                 250                 255 act gtg gcc gtt ata ctg aat tgt gga aat tca tca aga aca atc aca      816
Thr Val Ala Val Ile Leu Asn Cys Gly Asn Ser Ser Arg Thr Ile Thr
            260                 265                 270 ggt gat act tgt aat gag gag acc cag aat ctg agc aca ata tat ctc      864
Gly Asp Thr Cys Asn Glu Glu Thr Gln Asn Leu Ser Thr Ile Tyr Leu
        275                 280                 285 agg gaa tat caa tca aaa gtt aag agg cag ata ttt tca gac tat cag      912
Arg Glu Tyr Gln Ser Lys Val Lys Arg Gln Ile Phe Ser Asp Tyr Gln
    290                 295                 300 tca gag gtt gac ata tat aac aga att cgg gat gaa tta tga              954
Ser Glu Val Asp Ile Tyr Asn Arg Ile Arg Asp Glu Leu
305                 310                 315 ataaagtaaa atgttatgtt ttatttacgg cgttactatc ctctctatat gcacacggag   1014
ctccccagac tattacagaa ctatgttcgg aatatcgcaa cacacaaata tatacgataa   1074
atgacaagat actatcatat acggaatcga tggcaggcaa aagagaaatg gttatcatta   1134
catttaagag cggcgaaaca tttcaggtcg aagtcccggg cagtcaacat atagactccc   1194
agaaaaaagc cattgaaagg atgaaggaca cattaagaat cacatatctg accgagacca   1254
aaattgataa attatgtgta tggaataata aaacccccaa ttcaattgcg gcaatcagta   1314
tgaaaaacta g                                                        1325
```

<210> SEQ ID NO 2
<211> LENGTH: 317
<212> TYPE: PRT
<213> ORGANISM: Escherichia coli

<400> SEQUENCE: 2

```
Met Met Lys Cys Ile Leu Leu Lys Trp Ile Leu Cys Leu Leu Leu Gly
1               5                   10                  15

Phe Ser Ser Val Ser Tyr Ser Gln Glu Phe Thr Ile Asp Phe Ser Thr
            20                  25                  30

Gln Gln Ser Tyr Val Ser Ser Leu Asn Ser Ile Arg Thr Val Ile Ser
        35                  40                  45

Thr Pro Leu Glu His Ile Ser Gln Gly Ala Thr Ser Val Ser Val Ile
50                  55                  60

Asn His Thr Pro Pro Gly Ser Tyr Ile Ser Val Gly Ile Arg Gly Leu
65                  70                  75                  80

Asp Val Tyr Gln Glu Arg Phe Asp His Leu Arg Leu Ile Ile Glu Arg
                85                  90                  95

Asn Asn Leu Tyr Val Ala Gly Phe Val Asn Thr Thr Thr Asn Thr Phe
            100                 105                 110

Tyr Arg Phe Ser Asp Phe Ala His Ile Ser Leu Pro Gly Val Thr Thr
        115                 120                 125

Ile Ser Met Thr Thr Asp Ser Ser Tyr Thr Thr Leu Gln Arg Val Ala
130                 135                 140

Ala Leu Glu Arg Ser Gly Met Gln Ile Ser Arg His Ser Leu Val Ser
145                 150                 155                 160

Ser Tyr Leu Ala Leu Met Glu Phe Ser Gly Asn Thr Met Thr Arg Asp
                165                 170                 175

Ala Ser Arg Ala Val Leu Arg Phe Val Thr Val Thr Ala Glu Ala Leu
            180                 185                 190

Arg Phe Arg Gln Ile Gln Arg Glu Phe Arg Leu Ala Leu Ser Glu Thr
        195                 200                 205

Ala Pro Val Tyr Thr Met Thr Pro Glu Asp Val Asp Leu Thr Leu Asn
210                 215                 220

Trp Gly Arg Ile Ser Asn Val Leu Pro Glu Tyr Arg Gly Glu Ala Gly
225                 230                 235                 240

Val Arg Val Gly Arg Ile Ser Phe Asn Asn Ile Ser Ala Ile Leu Gly
                245                 250                 255

Thr Val Ala Val Ile Leu Asn Cys Gly Asn Ser Ser Arg Thr Ile Thr
            260                 265                 270

Gly Asp Thr Cys Asn Glu Glu Thr Gln Asn Leu Ser Thr Ile Tyr Leu
        275                 280                 285

Arg Glu Tyr Gln Ser Lys Val Lys Arg Gln Ile Phe Ser Asp Tyr Gln
        290                 295                 300

Ser Glu Val Asp Ile Tyr Asn Arg Ile Arg Asp Glu Leu
305                 310                 315
```

<210> SEQ ID NO 3
<211> LENGTH: 1325
<212> TYPE: DNA
<213> ORGANISM: Escherichia coli
<220> FEATURE:
<221> NAME/KEY: CDS
<222> LOCATION: (951)..(1322)

<400> SEQUENCE: 3

```
atgatgaagt gtatattgtt aaagtggata ctgtgtctgt tactgggttt ttcttcggta      60
tcctattccc aggagtttac gatagacttt tcgactcaac aaagttatgt atcttcgtta     120
aatagtatac ggacagtgat atcgacccct cttgaacata tatctcaggg agctacatcg     180
gtatccgtta ttaatcatac accaccagga agttatattt ccgtaggtat acgagggctt     240
gatgtttatc aggagcgttt tgaccatctt cgtctgatta ttgaacgaaa taatttatat     300
gtggctggat ttgttaatac gacaacaaat actttctaca gattttcaga ttttgcacat     360
atatcattgc ccggtgtgac aactatttcc atgacaacgg acagcagtta taccactctg     420
caacgtgtcg cagcgctgga acgttccgga atgcaaatca gtcgtcactc actggtttca     480
tcatatctgg cgttaatgga gttcagtggt aatacaatga ccagagatgc atcaagagca     540
gttctgcgtt ttgtcactgt cacagcagaa gccttacggt tcaggcaaat acagagagaa     600
tttcgtctgg cactgtctga aactgctcct gtttatacga tgacgccgga agacgtggac     660
ctcactctga actgggggag aatcagcaat gtgcttccgg agtatcgggg agaggctggt     720
gtcagagtgg ggagaatatc ctttaataat atatcagcga tacttggtac tgtggccgtt     780
atactgaatt gtggaaattc atcaagaaca atcacaggtg atacttgtaa tgaggagacc     840
cagaatctga gcacaatata tctcagggaa tatcaatcaa aagttaagag gcagatattt     900
tcagactatc agtcagaggt tgacatatat aacagaattc gggatgaatt atg aat       956
                                                         Met Asn
                                                           1 aaa gta aaa tgt tat gtt tta ttt acg gcg tta cta tcc tct cta tat     1004
Lys Val Lys Cys Tyr Val Leu Phe Thr Ala Leu Leu Ser Ser Leu Tyr
      5                  10                  15 gca cac gga gct ccc cag act att aca gaa cta tgt tcg gaa tat cgc     1052
Ala His Gly Ala Pro Gln Thr Ile Thr Glu Leu Cys Ser Glu Tyr Arg
 20                  25                  30 aac aca caa ata tat acg ata aat gac aag ata cta tca tat acg gaa     1100
Asn Thr Gln Ile Tyr Thr Ile Asn Asp Lys Ile Leu Ser Tyr Thr Glu
 35                  40                  45                  50 tcg atg gca ggc aaa aga gaa atg gtt atc att aca ttt aag agc ggc     1148
Ser Met Ala Gly Lys Arg Glu Met Val Ile Ile Thr Phe Lys Ser Gly
              55                  60                  65 gaa aca ttt cag gtc gaa gtc ccg ggc agt caa cat ata gac tcc cag     1196
Glu Thr Phe Gln Val Glu Val Pro Gly Ser Gln His Ile Asp Ser Gln
 70                  75                  80 aaa aaa gcc att gaa agg atg aag gac aca tta aga atc aca tat ctg     1244
Lys Lys Ala Ile Glu Arg Met Lys Asp Thr Leu Arg Ile Thr Tyr Leu
         85                  90                  95 acc gag acc aaa att gat aaa tta tgt gta tgg aat aat aaa acc ccc     1292
Thr Glu Thr Lys Ile Asp Lys Leu Cys Val Trp Asn Asn Lys Thr Pro
100                 105                 110 aat tca att gcg gca atc agt atg aaa aac tag                         1325
Asn Ser Ile Ala Ala Ile Ser Met Lys Asn
115                 120

<210> SEQ ID NO 4
<211> LENGTH: 124
<212> TYPE: PRT
<213> ORGANISM: Escherichia coli

<400> SEQUENCE: 4

Met Asn Lys Val Lys Cys Tyr Val Leu Phe Thr Ala Leu Leu Ser Ser
1               5                   10                  15

Leu Tyr Ala His Gly Ala Pro Gln Thr Ile Thr Glu Leu Cys Ser Glu
```

```
            20                  25                  30

Tyr Arg Asn Thr Gln Ile Tyr Thr Ile Asn Asp Lys Ile Leu Ser Tyr
            35                  40                  45

Thr Glu Ser Met Ala Gly Lys Arg Glu Met Val Ile Thr Phe Lys
 50                  55                  60

Ser Gly Glu Thr Phe Gln Val Glu Val Pro Gly Ser Gln His Ile Asp
 65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
                100                 105                 110

Thr Pro Asn Ser Ile Ala Ala Ile Ser Met Lys Asn
        115                 120

<210> SEQ ID NO 5
<211> LENGTH: 36
<212> TYPE: DNA
<213> ORGANISM: unknown
<220> FEATURE:
<223> OTHER INFORMATION: pimer no. 1832 in Table 1

<400> SEQUENCE: 5
aaaactgcag atgatgaagt gtatattgtt aaagtg                        36

<210> SEQ ID NO 6
<211> LENGTH: 40
<212> TYPE: DNA
<213> ORGANISM: unknown
<220> FEATURE:
<223> OTHER INFORMATION: primer no. 1833 in Table 1

<400> SEQUENCE: 6
gttcttgatg aatttccaca attcagtata acggccacag                    40

<210> SEQ ID NO 7
<211> LENGTH: 40
<212> TYPE: DNA
<213> ORGANISM: unknown
<220> FEATURE:
<223> OTHER INFORMATION: primer no. 1834 in table 1

<400> SEQUENCE: 7
ctgtggccgt tatactgaat tgtggaaatt catcaagaac                    40

<210> SEQ ID NO 8
<211> LENGTH: 33
<212> TYPE: DNA
<213> ORGANISM: unknown
<220> FEATURE:
<223> OTHER INFORMATION: primer no. 1835 in table no. 1

<400> SEQUENCE: 8
tcataattca tcccgaattc tgttatatat gtc                           33
```

HYBRID SHIGA-LIKE TOXIN

REFERENCE TO SEQUENCE LISTING

The material saved as "text document" under the file name "SubstituteSequenceListing" created on Nov. 11, 2008, is hereby incorporated by reference.

The present invention relates to a hybrid bacterial toxin subunit, to a hybrid bipartite bacterial toxin and to nucleic acid molecules comprising a nucleotide sequence encoding such bacterial toxins. Furthermore, the invention relates to vaccines comprising said bacterial toxins and to their use in vaccines, to methods for the preparation of such vaccines and to the use of such bacterial toxins for the manufacture of such vaccines.

BACKGROUND OF THE INVENTION

Many members of the Enterobacteriaceae such as *Shigella* and *Escherichia coli* are known to produce one or more toxins. Amongst these are several potent cytotoxins and neurotoxins. *Shigella dysenteriae* is known to produce the so-called Shiga-toxin (Sandvig, K., Toxicon 39: 1629-1635 (2001)). A group of very closely related *Escherichia coli* toxins is toxic to African green monkey (vero) cells, and thus they became known as verotoxins. These toxins show a close resemblance to a cytotoxic toxin that was earlier found in *Shigella dysenteriae* type 1, which explains their currently used name: Shiga-like toxins (SLT). The Shiga-like toxins have been described i.a. in a review by Agbodaze, D. (Comp. Immunol., Microbiol. & infectious diseases 22: 221-230 (1999)) and in a review by O'Brian, D. and Holmes, R. K. (Microbiol. Review 51: 206-220 (1987)).

It goes without saying that the invention is applicable to both the Shiga-toxin and the Shiga-like toxins. Shiga-like toxins are now known to be the cause of i.a. hemorrhagic colitis and hemolytic-uremic syndrome in humans (Karmali et al., Lancet I: 1299-1300 (1983)), diarrhea in calves (Chanter, N., Vet. Microbiol. 12: 241-253 (1986) and Mainil et al., Am. J. Vet. Res. 48: 734-748 (1987)) and edema disease in swine (Dobrescu, L., Am. J. Vet. Res. 44: 31-34 (1983), Gannon, V. P. J. at al., Can. J. Vet. Res. 53: 306-312 (1989), Marques, L. R. M., et al., FEMS Microbiol. Letters 44: 33-38 (1987), Smith, H. W. et al., J. Gen. Microbiol. 129: 3121-3137 (1983) and Smith, H. W. et al., J. Med. Microbiol. 1: 45-59 (1968)).

Clinical manifestations of edema in pigs, i.a. neurological dysfunction, result from microangiopathy and vascular necrosis caused by a specific Shiga-like toxin variant Stx2e (Neilsen, N, O., Edema Disease, p. 528-540 (1986) In A. D. Lehman, Straw, B., Glock R. D. et al. (ed.), Diseases of swine, 6$^{th}$ ed. Iowa State University Press, Ames. USA), (Gannon, V. P. J. at al., Can. J. Vet. Res. 53: 306-312 (1989), Kurtz, H. J. et al., Am. J. Vet. Res. 30: 791-806 (1969) and Marques, L. R. M., et al., FEMS Microbiol. Letters 44: 33-38 (1987)). This variant Stx2e, also known in the art as SLT-IIe, SLT-IIv, Verocytotoxin 2e and VT2e, causes a disease that strikes approximately one week following weaning. The disease, characterised by the edema and the subsequent specific neurological disturbances that it causes, is generally known as post-weaning edema (PWE) or edema disease.

Shiga-toxin and all Shiga-like toxins share the same general structure. They consist of a single A-subunit bound to multiple copies of a B-subunit. Normally, a single A-subunit is bound to a pentamer of B-subunits. The A-subunit is the actual toxin-part: it plays a role in the inhibition of the host's protein synthesis. The B-subunit, more specifically when in its pentamer form, is associated with receptor binding. A single B-subunit is about 7.5 kD, whereas the A-subunit is about 32 kD.

The DNA-sequence of the A1-part (see below) of the Shiga-like toxin variant Stx2e is provided in SEQ ID NO: 1.

FIG. 1: shows a schematic drawing of a typical Shiga-like toxin; its overall structure, the location of the A1/2 parts (see below) of the A-subunit and the location of the B-subunits.

The whole toxin is therefore best described as a bipartite toxin (i.e.: a toxin consisting of two parts) comprising a single A-subunit and single pentamer formed by 5 B-subunits. The A-subunit as such can subsequently be functionally divided into an A1-part being the actual enzymatic part, and an A2-part being the part of the A-subunit involved in binding to the pentamer of B-subunits. The binding of the A-subunit, through the A2-part of the A-subunit, to the B-subunit follows the lock-and-key principle: the A2-part of the A-subunit of Shiga-like toxin only fits into the B-subunit of Shiga-like toxin, and not to other, though closely related, B-subunits such as e.g. the B-subunit of the Heat-labile enterotoxin (LT) of *Escherichia coli*.

It is known that vaccination with inactivated toxins can be used to prevent disease caused by Shiga-like toxin producing *E. coli* strains. (Awad-Masalmeh, M., In Proc of the 10$^{th}$ Int. Pig Vet. Soc. Congress, R10 de Janeiro, Brazil (1988), Awad-Masalmeh, M., Dtsch. Tieraertzl. Wochenschr. 96: 419-421 (1989), Howard, J. G., Br. J. Exp. Pathol. 36: 439-4476 (1955), Islam, M. S., and Stimson, W. H., J. Clin. Lab. Immunol. 33: 11-16 (1990), MacLeod, D. L and Gyles, D. L., Vet. Microbiol. 29: 309-318 (1991), Wadolkowsky, E. A. et al., Infect. & Immun. 58: 3959-3965 (1990), Bosworth, B. T. Infect. & Immun. 64: 55-60 (1996)).

The genomic organisation as well as the location and sequence of the genes encoding the A- and B-subunits for Shiga-like toxins is known (Spicer E. K. et al., J. Biol. Chem, 257:5716-5721 (1982), Calderwood, S. B. et al., Proc. Natl. Acad. Sci. USA 84: 4364-4368 (1987), Dallas W. S. and Falkow S., Nature 288: 499-501 (1980), Leong J. et al., Infect. Immun. 48: 73-77 (1985)).

Therefore, in principle, having the necessary genetic information at hand, and knowing that vaccination with inactivated toxins can be used to prevent disease caused by Shiga-like toxin producing *E. coli* strains, large-scale in vitro expression of the genes encoding the A- and B-subunits seems a good starting point for vaccine production.

Against expectations however, although very efficient for the production and subsequent purification of both the A- and B-subunit of the comparable Heat-labile enterotoxin (LT) of *Escherichia coli* (see below), expression/purification turned out to be very difficult for Shiga-toxin and Shiga-like toxins.

First of all, although expression of the Shiga-like toxin B-subunit in a bacterial expression system is not a problem (Acheson et al., Infect. & Immun. 63: 301-308 (1995)), the Shiga-like toxin A-subunit can not, or only in minute quantities be expressed in bacterial expression systems.

Moreover, purification of the bipartite Shiga-toxin and Shiga-like toxin (contrary to the purification of LT) is both difficult and expensive. PCT-patent application WO 98/54215 provides ways of overcoming the difficulties experienced with purification, but relies therefore upon the use of affinity columns using expensive affinity ligands comprising disaccharides. For the preparation of a Shiga-toxin or Shiga-like toxin-based vaccine, this method of purification is from an economical point of view less desirable.

Therefore, both the expression and the purification of a Shiga-toxin or Shiga-like toxin remain problematic.

BRIEF SUMMARY OF THE INVENTION

It is an objective of the present invention to provide novel hybrid Shiga-toxin and Shiga-like toxins that do not suffer from the problems identified above.

Such novel hybrid Shiga-toxins and Shiga-like toxins differ from the known Shiga-like toxins in that they comprise the A1-part of the Shiga-like toxin, that is fused to the A2-part of the heat-labile enterotoxin (LT) of *Escherichia coli*. In the wild-type situation, the A1-part of the Shiga-like toxin is fused to the A2-part of the Shiga-like toxin.

It was surprisingly found now, that this hybrid Shiga- or Shiga-like A-subunit, contrary to its natural counterpart, can efficiently be expressed in bacterial expression systems. Also, it can easily and by inexpensive methods be purified. Moreover, this hybrid Shiga- or Shiga-like subunit comprising the A1-part of Shiga- or Shiga-like toxin but now fused to the A2-part of the LT is, even more surprisingly, fully capable of inducing protection against the wild-type Shiga- or Shiga-like toxin.

BRIEF DESCRIPTION OF THE FIGURES

FIG. 2: Construction of pMMB Stx2eA$_1$LTA$_2$B

Figure 1:
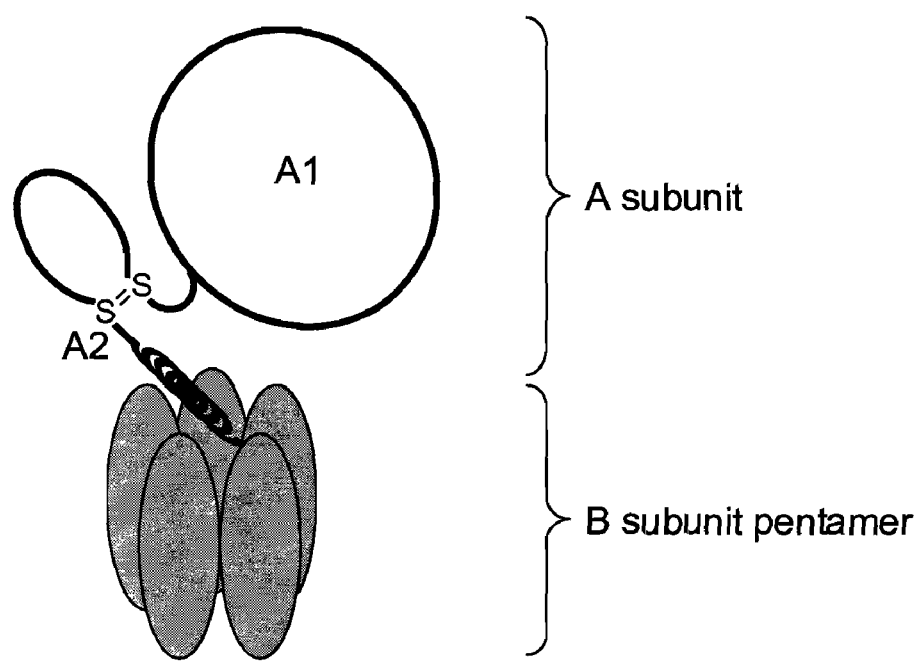
FIG. 1: Schematic drawing of a typical Shiga-like toxin; its overall structure, the location of the A1/2 parts of the A-subunit and the location of the B-subunits are shown.

Lane 1: prestained marker; lane 2: whole culture pMMB Stx2eA$_1$LTA$_2$B after induction; lane 3: non bound fraction; lane 4: wash volume 1; lane 5: wash volume 5; lane 6: purified Stx2eA$_1$LTA$_2$B eluate 1; lane 7: purified Stx2eA$_1$LTA$_2$B eluate 2; lane 8: purified Stx2eA$_1$LTA$_2$B eluate 3; lane 9: purified Stx2eA$_1$LTA$_2$B eluate 4; lane 10: purified Stx2eA$_1$LTA$_2$B eluate 5; lane 11: purified Stx2eA$_1$LTA$_2$B eluate 6; lane 12: purified Stx2eA$_1$LTA$_2$B eluate 7 lane 13: purified Stx2eA$_1$LTA$_2$B eluate 8

DETAILED DESCRIPTION OF THE INVENTION

Heat-labile enterotoxin (LT) of *Escherichia coli*, like the Shiga-like toxin of *Escherichia coli*, is a bacterial protein toxin with a AB5 multimer structure, in which the B pentamer has a membrane binding function and the A subunit is needed for enzymatic activity (Fukuta, S. et al., Inf. & Immun. 56: 1748-1753 (1988), Pickett, C. L. et al., J. Bacteriol. 165: 348-352 (1986), Okamoto, K. et al., J. Bacteriol. 180: 1368-1374 (1998) and Lea, N. et al., Microbiology 145: 999-004 (1999)).

The expression "fused to" means that the amino acid sequence constituting the A1-part is covalently bound to the amino acid sequence constituting the A2-part. This means that the final subunit forms a single protein, as is the case in the wild-type situation.

Therefore, one embodiment of the present invention relates to a hybrid bacterial toxin A-subunit that comprises an A1-part of Shiga-like toxin fused to an A2-part of *Escherichia coli* heat-labile enterotoxin (LT).

The boundaries of the A1- and the A2-part of the A-subunit can be drawn quite precise for both the Shiga-like toxin and for LT. The A1- and A2-part are bound together by a short loop between two disulphide-linked cysteines. It is this loop that connects the A1-part and the A2-part. After entrance of the LT or Shiga-like toxin in the mammalian cell, a cleavage occurs in this loop, during which the (in the case of Shiga-like toxin 27.5 kD) A1-part and (in the case of Shiga-like toxin 4.5 kD) A2-part become separated (Okamoto, K. et al., J. Bacteriol. 180: 1368-1374 (1998) and Lea, N. et al., Microbiology 145: 999-004 (1999)).

In the sequence as depicted in SEQ ID NO: 1 an example of the nucleic acid sequence of a hybrid A-subunit according to the invention comprising the Stx2e A1 part and the LT-A2-part is shown. The amino acid sequence of the hybrid bacterial toxin encoded by this sequence is depicted in SEQ ID NO. 2.

The nucleic acid sequence encoding the hybrid A-subunit starts at position 1 and stops at position 951. In this example, the Stx2e A1-part of the A subunit starts at nucleic acid position 1 and ends at position 789, and thus just upstream the first of the disulphide-linked cysteines. The LT-A2-part of the A subunit starts at nucleic acid position 790 and ends at position 951.

The disulphide-linked cysteine residues are coded for at respectively positions 790-792 and 826-828.

The A1-part can therefore also be referred to as the part that is located at the N-terminal side of the loop, whereas the A2-part can be referred to as the part that is located at the C-terminal side of the loop.

It is clear that in principle the transition point between the A1-part and the A2-part is not critical. In the example given above, the transition point is located just upstream the first of disulphide-linked cysteines. It could however equally well be located somewhere between the two cysteine residues or just downstream of the second disulphide-linked cysteine at position 826-828. Actually, there is only one prerequisite: the A1-part must be capable to provide immunity against the Shiga-like toxin and the A2-part must be capable of binding to the LT-pentamer. Even more, there is no need to maintain, in the hybrid A-subunit according to the invention, the proteolytic cleavage site in the A-subunit, since this plays no role in the induction of immunity.

Additionally, it is shown in SEQ ID No: 3 where the LT-B subunit is located. The nucleotide sequence encoding this subunit starts at position 951 and ends at position 1322. Of course it is beneficial to have the nucleotide sequences encoding the hybrid A-subunit according to the invention and the LT-B-subunit at one and the same plasmid, as is the case in this example. Such a plasmid provides at the same time the genetic information for both the A- and the B-subunit of the bipartite bacterial toxin according to the invention.

The coding sequences can be brought under the control of one and the same promoter, as is the case in SEQ ID No: 1. But if further fine-tuning of the ratio hybrid A-subunit versus LT-B-subunit is required, it could be beneficial to bring the expression of both under the control of two different promoters.

The invention is applicable to Shiga-toxin and all Shiga-like toxin variants. These variants include those found to cause disease in humans as well as those causing disease in animals as is described above.

Since it is known that the Shiga-like toxin variant Stx2e causes post-weaning disease in pigs, this variant clearly is an attractive candidate for use in vaccines for pig industry. Thus, a preferred form of this embodiment relates to hybrid A-subunits in which the A1-part of the A-subunit is an A1-part of Stx2e.

Especially beneficial is the expression of the hybrid toxin A-subunit according to the invention in the presence of the gene encoding the B-subunit of the heat-labile enterotoxin. This was already mentioned above. Expression of both the hybrid A-subunit hybrid Shiga-like toxin according to the invention and the heat-labile enterotoxin in the same cell leads to spontaneous formation of the hybrid bipartite bacterial toxin, i.e. a toxin having the A1-part of Shiga-like toxin fused to the A2-part of LT, and bound to the B-subunit of LT.

The hybrid bipartite toxin so made can first of all be easily expressed, secondly has the immunogenic properties of Shiga-like toxin, in the sense that it can be used for the induction of protection against the Shiga-like toxin, and thirdly has the advantage that it can easily be purified according to methods known for the purification of LT (Uesaka, Y., at al., Microb. Pathog. 16: 71-76 (1994)).

Therefore, a more preferred form of this embodiment relates to a hybrid bipartite bacterial toxin comprising five B-subunits of *Escherichia coli* heat-labile enterotoxin (LT) and the hybrid bacterial toxin A-subunit according to the invention.

It is clear that, because the nucleotide sequences of the genes encoding the A-subunits and B-subunits of both Shiga-like toxin and LT are known, standard techniques for genetic engineering suffice to construct a nucleotide sequence encoding the hybrid toxin subunit A according to the invention. One way of engineering such a nucleotide sequence is given in the Examples. Man skilled in the art finds sufficient guidance, if necessary at all, in this Example to make comparable nucleotide sequences encoding other Shiga-like toxin variants according to the invention.

Thus another embodiment of the present invention relates to a nucleic acid molecule comprising a nucleotide sequence encoding a hybrid bacterial toxin subunit according to the invention.

It would be even more beneficial to additionally add to such nucleotide sequence the nucleotide sequence encoding the B-subunit of LT. Expression of such a combined nucleotide sequence in a cell would lead to the simultaneous production of the hybrid toxin A-subunit according to the invention and the LT B-subunit. This in turn leads to the auto-formation of the hybrid bipartite bacterial toxin according to the invention. Below it is indicated how expression of the encoded proteins can in practice be effectuated.

Although efficient, it is however not necessary for the genetic information encoding the hybrid A-subunit and the B-subunit to be on the same nucleotide sequence. Merely as an example; the genetic information for each of the two subunits could be located on its own plasmid. A host cell comprising both plasmids would be capable to form the hybrid bipartite bacterial protein according to the invention. It is even possible to synthesize both subunits in different bacteria, to isolate them and to bring them together under renaturing conditions after isolation.

Expression of the hybrid bacterial toxin subunit can e.g. be done by using commercially available expression systems.

Therefore, in a more preferred form of this embodiment, the invention relates to DNA fragments comprising a nucleic acid molecule comprising a nucleotide sequence encoding a hybrid bacterial toxin subunit according to the invention. A DNA fragment is a stretch of nucleotides that functions as a carrier for a nucleic acid molecule comprising a nucleotide sequence according to the invention. Such DNA fragments can e.g. be plasmids, into which a nucleic acid molecule comprising a nucleotide sequence encoding a hybrid bacterial toxin subunit according to the invention is cloned. Such DNA fragments are e.g. useful for enhancing the amount of DNA and for expression of a nucleic acid molecule comprising a nucleotide sequence encoding a hybrid bacterial toxin subunit according to the invention, as described below.

An essential requirement for the expression of the nucleic acid molecule comprising a nucleotide sequence encoding a hybrid bacterial toxin subunit is an adequate promoter functionally linked to the nucleic acid molecule comprising that nucleotide sequence, so that the nucleic acid molecule comprising the nucleotide sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment and/or a nucleic acid molecule comprising a nucleotide sequence encoding a hybrid bacterial toxin subunit according to the invention wherein the nucleic acid molecule comprising a nucleotide sequence encoding a hybrid bacterial toxin subunit according to the invention is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6).

Functionally linked promoters are promoters that are capable of controlling the transcription of the nucleic acid molecule comprising a nucleotide sequences to which they are linked.

Such a promoter can be the native promoter of the Shiga-like toxin or another promoter of *E. coli*, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of vertebrate origin illustrative useful expression control sequences include the (human) cytomegalovirus immediate early promoter (Seed, B. et al., Nature 329, 840-842, 1987; Fynan, E. F. et al., PNAS 90, 11478-11482,1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well known bovine growth hormone poly-adenylation sequence, the SV40 poly-adenylation sequence, the human cytomegalovirus (hCMV) terminator and poly-adenylation sequences.

Bacterial, yeast, fungal, insect and vertebrate cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are attractive expression systems. Such systems are e.g. described in the French Patent Application with Publication number 2 714 074, and in US NTIS Publication Ser. No. 08/043,109 (Hoffman, S, and Rogers, W.: Public. Date 1 Dec. 1993).

A still even more preferred form of this embodiment of the invention relates to Live Recombinant Carriers (LRCs) comprising a nucleic acid molecule comprising a nucleotide sequence encoding the hybrid bacterial toxin subunit according to the invention, a DNA fragment according to the invention or a recombinant DNA molecule according to the invention. These LRCs are micro-organisms or viruses in which additional genetic information, in this case a nucleic acid molecule comprising a nucleotide sequence encoding the hybrid subunit according to the invention, has been cloned. Pigs infected with such LRCs will produce an immunological response not only against the immunogens of the carrier, but also against the immunogenic parts of the protein(s) for which the genetic code is additionally cloned into the LRC, e.g. the novel hybrid bacterial toxin subunit according to the invention.

As an example of bacterial LRCs, attenuated *Salmonella* strains known in the art can very attractively be used.

Also, live recombinant carrier parasites have i.a. been described by Vermeulen, A. N. (Int. Journ. Parasitol. 28: 1121-1130 (1998)).

Furthermore, LRC viruses may be used as a way of transporting the nucleic acid molecule comprising a nucleotide sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E. P. A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic acid molecule into the genome of a bacterium, parasite or virus of choice, capable of inducing expression of the inserted nucleotide sequence according to the invention in the host animal.

Finally another form of this embodiment of the invention relates to a host cell comprising a nucleic acid molecule comprising a nucleotide sequence encoding a hybrid bacterial toxin subunit according to the invention, a DNA fragment comprising such a nucleic acid molecule or a recombinant DNA molecule comprising such a nucleic acid molecule under the control of a functionally linked promoter. This form also relates to a host cell containing a live recombinant carrier comprising a nucleic acid molecule comprising a nucleotide sequence encoding a hybrid bacterial toxin subunit according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Since it is now for the first time possible to make, in in vitro expression systems, sufficient amounts of hybrid toxin subunit A and hybrid bipartite toxin according to the invention, is becomes feasible to make vaccines based upon these hybrid toxins.

Vaccines based upon the expression products of these genes can easily be made by admixing the toxins according to the invention with a pharmaceutically acceptable carrier as described below.

If necessary, the toxin may be detoxified according to techniques known in the art, e.g. by formalin-treatment.

Therefore, another embodiment of the invention relates to vaccines comprising a hybrid bacterial toxin according to the invention or a hybrid bipartite bacterial toxin according to the invention, and a pharmaceutically acceptable carrier.

Another embodiment of the invention relates to the use of a hybrid bacterial toxin subunit or a hybrid bipartite bacterial toxin according to the invention for the manufacture of a vaccine for combating *Shigella* or *Escherichia coli* infection.

Alternatively, a vaccine according to the invention can comprise live recombinant carriers as described above, capable of expressing the protein according to the invention. Such vaccines, e.g. based upon a *Salmonella* carrier or a viral carrier e.g. a Herpesvirus vector have the advantage over subunit vaccines that they better mimic the natural way of infection of *Shigella* or *Escherichia coli*. Moreover, their self-propagation is an advantage since only low amounts of the recombinant carrier are necessary for immunization.

Vaccines can also be based upon host cells as described above, that comprise a bacterial toxin according to the invention.

Therefore, another form of the vaccine embodiment relates to vaccines comprising a live recombinant carrier according to the invention or a host cell according to the invention, and a pharmaceutically acceptable carrier.

Still another embodiment of the invention relates to the use of a live recombinant carrier or a host cell according to the invention for the manufacture of a vaccine for combating *Shigella* or *Escherichia coli* infection.

Still another embodiment of the present invention relates to the hybrid bacterial toxin subunit A or the hybrid bipartite toxin according to the invention for use in a vaccine.

Still another embodiment of the present invention relates to a live recombinant carrier or a host cell according to the invention for use in a vaccine.

All vaccines described above contribute to active vaccination, i.e. they trigger the host's defense system.

Alternatively, antibodies can be raised in e.g. rabbits or can be obtained from antibody-producing cell lines as described below. Such antibodies can then be administered to the human or animal to be protected. This method of vaccination, passive immunization, is the vaccination of choice when an animal is already infected, and there is no time to allow the natural immune response to be triggered. It is also the preferred method for vaccinating animals that are prone to sudden high infection pressure. The administered antibodies against the protein according to the invention or immunogenic fragments thereof can in these cases bind directly to Shiga-like toxin. This has the advantage that it decreases or stops the damaging effects of infection with *Shigella* or *E. coli* making Shiga-like toxins.

Therefore, one other form of this embodiment of the invention relates to a vaccine for combating *Shigella* or *Escherichia*

*coli* infection that comprises antibodies against the hybrid bacterial toxins according to the invention, and a pharmaceutically acceptable carrier.

Still another embodiment of this invention relates to antibodies against the hybrid toxins according to the invention.

Methods for large-scale production of antibodies according to the invention are also known in the art. Such methods rely on the cloning of (fragments of) the genetic information encoding the protein according to the invention in a filamentous phage for phage display. Such techniques are described i.a., in review papers by Cortese, R. et al., (1994) in Trends Biotechn. 12: 262-267., by Clackson, T. & Wells, J. A. (1994) in Trends Biotechn. 12: 173-183, by Marks, J. D. et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S, and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

Still another embodiment relates to a method for the preparation of a vaccine according to the invention that comprises the admixing of antibodies against a hybrid bacterial toxin according to the invention and a pharmaceutically acceptable carrier.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)). This way of vaccination is also attractive for the vaccination of humans and animals against infection with a *Shigella* or *Escherichia coli* strain producing a Shiga-like toxin.

Therefore, still other forms of this embodiment of the invention relate to vaccines comprising nucleic acid molecule comprising a nucleotide sequence encoding a hybrid toxin according to the invention, DNA fragments according to the invention or recombinant DNA molecules according to the invention, and a pharmaceutically acceptable carrier.

Examples of DNA plasmids that are suitable for use in a DNA vaccine according to the invention are conventional cloning or expression plasmids for bacterial, eukaryotic and yeast host cells, many of said plasmids being commercially available. Well-known examples of such plasmids are pBR322 and pcDNA3 (Invitrogen). The DNA fragments or recombinant DNA molecules according to the invention should be able to induce protein expression of the nucleic acid molecule comprising a nucleotide sequence. The DNA fragments or recombinant DNA molecules may comprise one or more nucleotide sequences according to the invention. In addition, the DNA fragments or recombinant DNA molecules may comprise other nucleic acid molecules comprising a nucleotide sequence such as the immune-stimulating oligonucleotides having unmethylated CpG di-nucleotides, or nucleotide sequences that code for other antigenic proteins or adjuvating cytokines.

The nucleic acid molecule comprising a nucleotide sequence according to the present invention or the DNA plasmid comprising a nucleic acid molecule comprising a nucleotide sequence according to the present invention, preferably operably linked to a transcriptional regulatory sequence, to be used in the vaccine according to the invention can be naked or can be packaged in a delivery system. Suitable delivery systems are lipid vesicles, iscoms, dendromers, niosomes, polysaccharide matrices and the like, (see further below) all well-known in the art. Also very suitable as delivery system are attenuated live bacteria such as *Salmonella* species, and attenuated live viruses such as Herpesvirus vectors, as mentioned above.

DNA vaccines can e.g. easily be administered through intradermal application such as by using a needle-less injector. This way of administration delivers the DNA directly into the cells of the animal to be vaccinated. Amounts of DNA in the range between 10 pg and 1000 μg provide good results. Preferably, amounts in the microgram range between 1 and 100 μg are used.

Another embodiment of the present invention relates to a nucleic acid molecule comprising a nucleotide sequence according to the invention, DNA fragments according to the invention, or recombinant DNA molecules according to the invention for use in a vaccine.

Still another embodiment of the present invention relates to the use of a nucleic acid molecule comprising a nucleotide sequence, a DNA fragment or a recombinant DNA molecule according to the invention for the manufacturing of a vaccine for combating *Shigella* or *Escherichia coli* infection.

In a further embodiment, the vaccine according to the present invention additionally comprises one or more antigens derived from pathogenic organisms and viruses, antibodies against those antigens or genetic information encoding such antigens. Of course, such antigens can be e.g. other *Shigella* or *Escherichia coli* antigens. It can also be an antigen selected from another other pig pathogenic organism or virus. In cases where the vaccine is used for vaccination of pigs, such organisms and viruses are preferably selected from the group of Pseudorabies virus, Porcine influenza virus, Porcine parvo virus, Transmissible gastro-enteritis virus, Rotavirus, *Erysipelothrix rhusiopathiae, Bordetella bronchiseptica, Brachyspira hyodysenteriae, Shigella* sp., *Salmonella choleraesuis, Salmonella typhimurium, Salmonella enteritidis, Haemophilus parasuis, Pasteurella multocida, Streptococcus suis, Mycoplasma hyopneumoniae, Actinobacillus pleuropneumoniae, Staphylococcus hyicus* and *Clostridium perfringens.*

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein according to the invention and/or antibodies against that protein or an immunogenic fragment thereof, and/or a nucleic acid molecule comprising a nucleotide sequence and/or a DNA fragment, a recombinant DNA molecule, a live recombinant carrier or host cell according to the invention, and a pharmaceutically acceptable carrier.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in pig vaccines are muramyldipeptides, lipopolysaccharides, several glucans and glycans and CARBOPOL® (a homopolymer).

The vaccine may also comprise a so-called "vehicle". A vehicle is a compound to which the protein adheres, without being covalently bound to it. Such vehicles are i.a. bio-microcapsules, micro-alginates, liposomes and macrosols, all known in the art. A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g., SPAN or TWEEN.

Often, the vaccine is mixed with stabilisers, e.g. to protect degradation-prone proteins from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent. It goes without saying, that other ways of adjuvating, adding vehicle compounds or diluents, emulsifying or stabilising a protein are also embodied in the present invention.

Vaccines based upon the bacterial toxins and/or subunits according to the invention can very suitably be administered in amounts ranging between 1 and 100 micrograms of protein per animal, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Vaccines according to the invention can be administered e.g. intradermally, subcutaneously, intramuscularly, intraperitoneally, intravenously, or at mucosal surfaces such as orally or intranasally.

Still another embodiment of the invention relates to methods for the preparation of a vaccine according to the invention which method comprises the admixing of a hybrid bacterial toxin subunit or a hybrid bipartite bacterial toxin according to the invention and a pharmaceutically acceptable carrier.

Still another embodiment of the invention relates to methods for the preparation of a vaccine according to the invention which method comprises the admixing of a nucleic acid sequence, a DNA fragment or a recombinant DNA molecule according to the invention and a pharmaceutically acceptable carrier.

Finally, another embodiment of the invention relates to methods for the preparation of a vaccine according to the invention which method comprises the admixing of a live recombinant carrier or a host cell according to the invention or antibodies against a hybrid (bipartite) bacterial toxin according to the invention and a pharmaceutically acceptable carrier.

EXAMPLES

Example 1

Construction of Expression Plasmid

Bacterial Strains and Plasmids

E. coli host strain BL21(DE3)star, HMS174(DE3) and BL21codon+RIL(DE3) were purchased from Novagen (Madison, Wis., USA). E. coli strain TOP10F' and plasmid pCR2.1—TOPO TA and pCR-bluntII-TOPO were purchased from Invitrogen (Groningen, the Netherlands).

Plasmid pMMB66HE has been described by Furste, J. P. et al., in Gene 48: 119-131 (1986).

PCR Amplification and Cloning of PCR Products

PCR on E. coli chromosomal DNA was performed with the SUPERTAQ PLUS DNA polymerase. The PCR mixture contained 20 U/ml SUPERTAQ PLUS (HT Biotechnology Ltd, Cambridge, UK), SUPERTAQ buffer containing (HT Biotechnology Ltd, Cambridge, UK), 8 mM dNTPs (Promega, Wis., USA), 10 pmoles of primers and 15 ng chromosomal DNA of E. coli as DNA template. Oligonucleotide sequences of all primers used for amplification of DNA are listed in table 1. PCR products were separated on agarose gel and gel purified using Qiagen PCR purification kit (Qiagen Inc., California, USA). Overlap extension PCR was performed as described in Sambrook et al. (Maniatis/Sambrook (Sambrook, J. Molecular cloning: a laboratory manual, 1989. ISBN 0-87969-309-6)). PCR products were cloned into pCR-bluntII-topo using the TOPO cloning kit (Invitrogen., Groningen, the Netherlands). Cloning reactions were performed according to manufacturers instructions.

Construction of OMB $Stx2eA_1LTA_2B$ $Stx2eA_1$ was amplified by PCR using primers #1832 and #1833 (see table 1) with EDNL50 chromosomal DNA as template using high fidelity polymerase. EDNL50 was isolated from a pig diagnosed with post weaning edema disease. Any other strain producing Shiga-like toxin could for that matter have been used equally well. $LTA_2LTB$ including the disulphide bridge was amplified using primers #1834 and #1835 (see table 1) with plasmid pMMB66-LT as template using high fidelity polymerase. Again; any other strain producing LT could for that matter have been used equally well. One microliter of each PCR was used in the overlap extension PCR product was made using primers #1832 and #1835. The obtained PCR product and pMMB66HE were digested with PstI and BamHI and subsequently ligated resulting in pMMB $Stx2eA_1LTA_2B$. The plasmid was checked by nucleotide sequence analysis and no artifacts were found.

Figure 2:
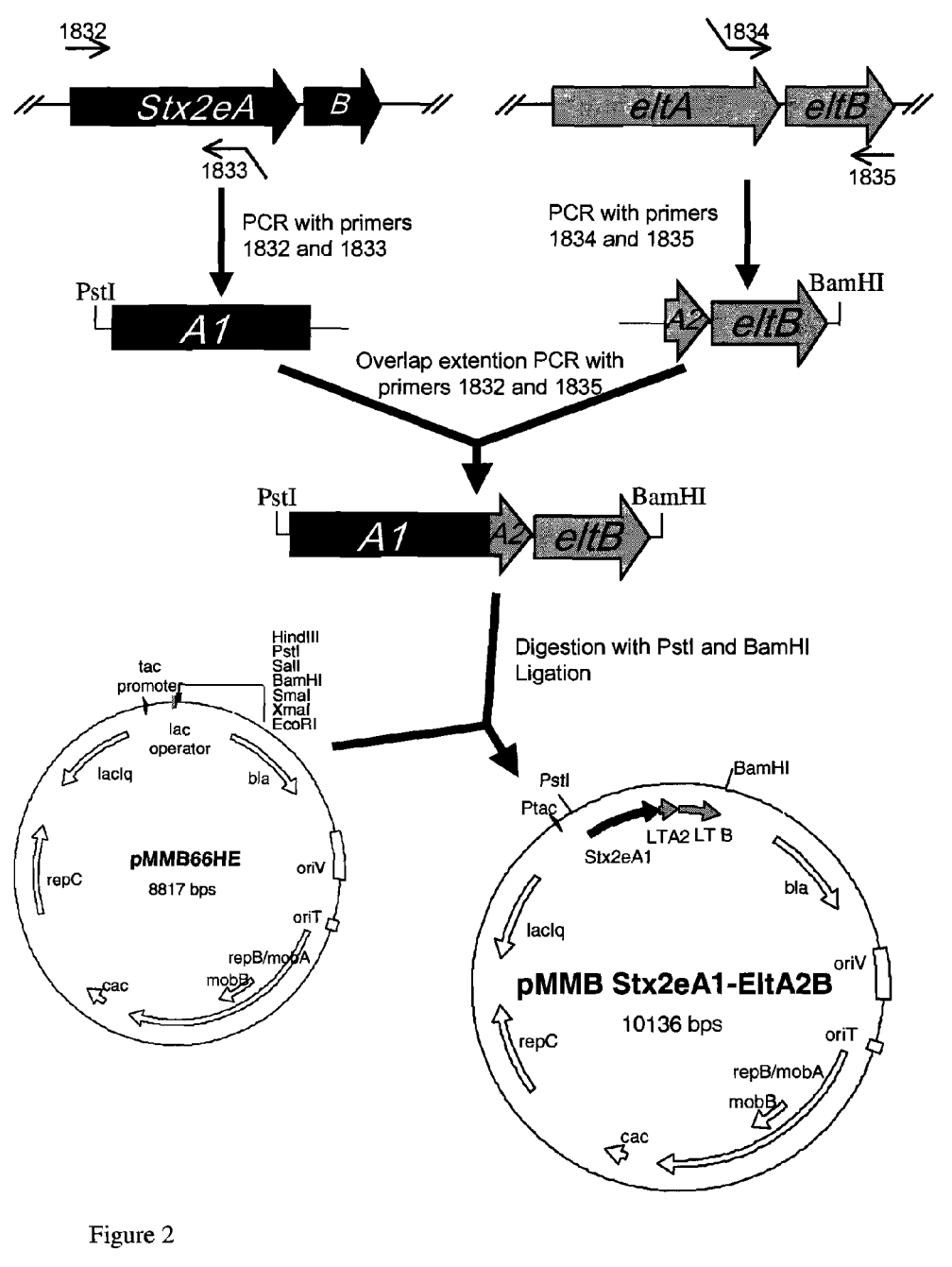

FIG. 2 shows the construction scheme of pMMB $Stx2eA_1LTA_2B$.

TABLE 1

| | |
|---|---|
| 1832 | AAAACTGCAGATGATGAAGTGTATATTGTTAAAGTG |
| 1833 | GTTCTTGATGAATTTCCACAATTCAGTATAACGGCCACAG |
| 1834 | CTGTGGCCGTTATACTGAATTGTGGAAATTCATCAAGAAC |
| 1835 | TCATAATTCATCCCGAATTCTGTTATATATGTC |

Example 2

Expression and Purification of $Stx2eA_1LTA_2B$

Expression of Recombinant Protein

E. coli expression strains containing a tac promoter based expression vector were grown overnight at 37° C. at 200 rpm in 5 ml TB with the appropriate antibiotics and 10 mM $MgSO_4$. The following morning the overnight cultures were diluted 1:100 in 5 ml TB with the appropriate antibiotics. These cultures were grown under the same conditions until an $OD_{600}$ of 0.5 was reached, measured on a NOVASPEC II spectrophotometer (Pharmacia, Woerden, the Netherlands). At this point, the cultures were induced by the addition of IPTG to a final concentration of 1 mM and followed by an additional incubation at 37° C. for 3 hours. 100 µl samples were taken for analysis at the beginning and end of the final incubation and of the appropriate controls. The samples were analyzed by SDS page, followed by a COOMASSIE BRILLIANT BLUE staining. The remaining culture was centrifuged at 5,000 rpm and the pellet was stored at −20° C. until further use.

Polyacrylamide Gel Electrophoresis and Western Blotting

SDS-PAGE was performed using 4-12% Bis-Tris gels from the NuPAGE electrophoresis system (Novex, San Diego, USA). Before separation the samples were boiled for 5 minutes with sample buffer (sample:buffer=2:1) in the presence of B-mercapto-ethanol in order to get a denatured protein profile. For the separation of non-denatured protein, sample buffer without B-mercapto-ethanol was added to the samples. These samples loaded onto the gel without heating. The gels were stained with COOMASSIE BRILLIANT BLUE or blotted onto IMMUNOBULON-P-MEMBRANE (Millipore, Bedford, USA) by standard semi-dry Western blotting procedures.

Rabbit anti-LT polyclonal α0508/09HRP and rabbit anti-LT polyclonal α0506/07 were raised against formaline inactivated LT. The anti LT-A monoclonal was purchased from Biotrend (Köln, Germany). LT(K8425) used as positive control was from a production batch. The LT was galactose-silica purified from culture supernatant and galactose used for elution was removed by dialysis. The final product contained 156 mg/l LT.

Galactose Purification of Expressed Proteins 5 ml induced culture was sonicated (Branson sonifier, Geneva, Switzerland) at duty cycle 50% and microtip to complete lysis. The lysate was centrifuged for 5 minutes at 6,000 rpm to remove insoluble protein. The cleared supernatant was applied to a 1 ml galactose-silica column. Column material was supplied by Organon (Oss, the Netherlands). This column was pre-equilibrated with 10 volumes of TEAN buffer (50 mM Tris, 1 mM EDTA, 3 mM Na-azide, 200 mM NaCl, pH 7.5). After binding of the supernatant, the column was washed with 5 volumes of TEAN buffer. Purified protein was eluted with 0.5 M galactose and stored at 4° C. until further use.

RESULTS

Expression of $Stx2eA_1LTA_2B$ Fusion Protein

Three E. coli expression strains were tested for expression of the fusion protein. Construct pMMB $Stx2eA_1LTA_2B$ was brought into B121star(DE3), HMS174(DE3) and JA221 and induced as described. Expression strain B121star(DE3) gave the highest expression level (data not shown).

Identification of $Stx2eA_1LTA_2$ Using Western Blotting

SDS-PAAGE-gels described above were blotted onto IMMOBULON—P-MEMBRANE (Millipore, Bedford, USA) by standard semi-dry Western blotting procedures.

Rabbit anti-LT polyclonal α0506/07 to develop the blot was raised against formaline inactivated LT. LT used as positive control was purified from culture supernatant using affinity chromatography (galactose-silica).

Figure 3:
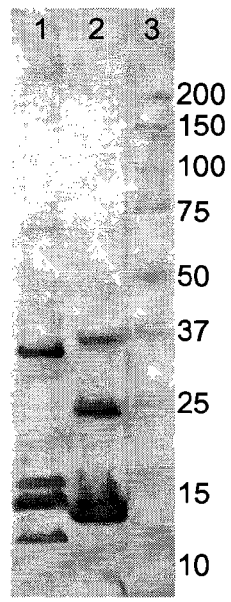
FIG. 3: Western blot developed with anti LT serum Lane 1: Stx2eA$_1$LTA$_2$B; lane 2: LTA/B; lane 3: prestained marker

As can be seen from FIG. 3, lane 2, both LT subunits reacted with the polyclonal antiserum: LTA (26 kDa) and LTB (14A kDa). This latter band is as expected also seen in lane 1 that contains the expression products of pMMB $Stx2eA_1LTA_2B$. The presence of LTA2 fragment in $Stx2eA_1LTA_2$ was sufficient to obtain a clearly visible $Stx2eA_1LTA_2$ band in lane 1 at the expected size (35.1 kDa).

Galactose Purification of $Stx2eA_1LTA_2B$

Figure 4:
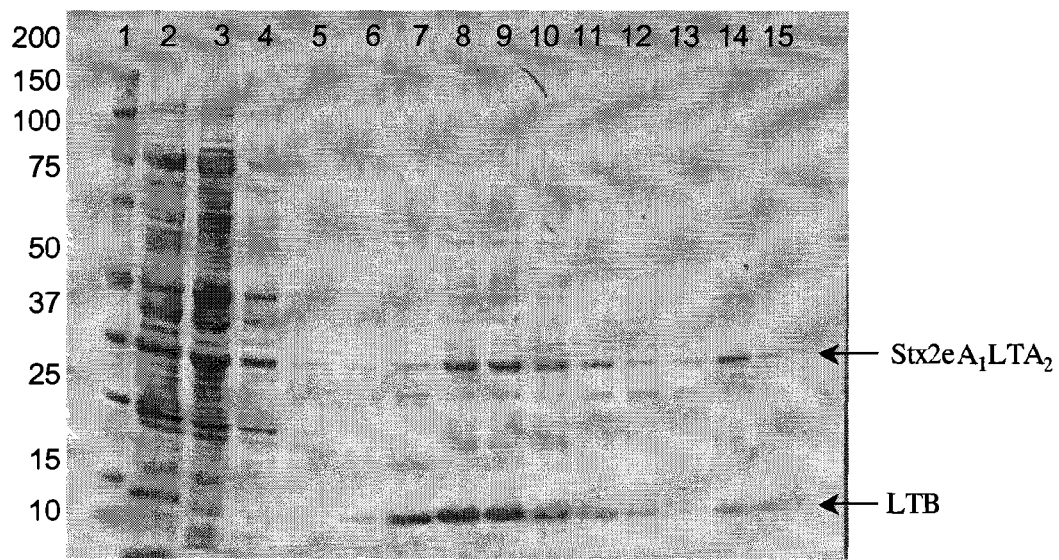
FIG. 4: Galactose-silica purification. PAAGE-gel, coomasie-stained.

PMMB $Stx2eA_1LTA_2B$ was induced as described and the $Stx2eA_1LTA_2B$ fusion protein was purified from bacterial pellet by galactose purification. Results are shown in FIG. 4. This figure shows the amount and purity of the $Stx2eA_1LTA_2B$ expression products in the various fractions of the galactose-silica column: lane 1: prestained marker; lane 2: whole culture pMMB $Stx2eA_1LTA_2B$ after induction; lane 3: non bound fraction; lane 4: wash volume 1; lane 5: wash volume 5; lane 6: purified $Stx2eA_1LTA_2B$ eluate 1; lane 7: purified $Stx2eA_1LTA_2B$ eluate 2; lane 8: purified $Stx2eA_1LTA_2B$ eluate 3; lane 9: purified $Stx2eA_1LTA_2B$ eluate 4; lane 10: purified $Stx2eA_1LTA_2B$ eluate 5; lane 11: purified $Stx2eA_1LTA_2B$ eluate 6; lane 12: purified $Stx2eA_1LTA_2B$ eluate 7 lane 13: purified $Stx2eA_1LTA_2B$ eluate 8.

The invention claimed is:

1. A hybrid bacterial toxin subunit comprising an A1-part and an A2-part fused together, wherein the A1-part is the A1-part of Shiga-toxin or Shiga-like toxin and the A2-part is the A2-part of *Escherichia coli* heat-labile enterotoxin.

2. The hybrid bacterial toxin subunit according to claim 1, wherein the A1-part is the A1-part of Stx2e.

3. A hybrid bipartite bacterial toxin comprising five B-subunits of *Escherichia coli* heat-labile enterotoxin and the hybrid bacterial toxin subunit according to claim 1.

4. A vaccine comprising the hybrid bacterial toxin subunit according to claim 1 and a pharmaceutically acceptable carrier.

5. The vaccine according to claim 4, wherein said vaccine further comprises an additional antigen of a micro-organism pathogenic to animals.

6. The vaccine according to claim 5, wherein said vaccine comprises *Escherichia coli*.

7. A method for the preparation of a vaccine, said method comprising the admixing of
    the hybrid bacterial toxin subunit according to claim 1 and
    a pharmaceutically acceptable carrier.

8. The hybrid bipartite bacterial toxin of claim 3, wherein the A1-part of the hybrid bacterial toxin subunit is the A1-part of Stx2e.

9. The vaccine of claim 4, wherein the A1-part of the hybrid bacterial toxin subunit is the A1-part of Stx2e.

10. The method of claim 7, wherein the A1-part of the hybrid bacterial toxin subunit is the A1-part of Stx2e.

* * * * *